US009613446B2

(12) United States Patent
Fox et al.

(10) Patent No.: US 9,613,446 B2
(45) Date of Patent: *Apr. 4, 2017

(54) OBSCURED RELATIONSHIP DATA WITHIN A GRAPH

(71) Applicant: International Business Machines Corporation, Armonk, NY (US)

(72) Inventors: Joshua Fox, Emek Haela (IL); Itai Gordon, Jerusalem (IL)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/296,534

(22) Filed: Jun. 5, 2014

(65) Prior Publication Data

US 2015/0187104 A1  Jul. 2, 2015

Related U.S. Application Data

(63) Continuation of application No. 14/141,045, filed on Dec. 26, 2013.

(51) Int. Cl.
  *G06T 11/20* (2006.01)
  *G06F 19/00* (2011.01)

(52) U.S. Cl.
  CPC ............ *G06T 11/206* (2013.01); *G06F 19/30* (2013.01)

(58) Field of Classification Search
  None
  See application file for complete search history.

(56) References Cited

U.S. PATENT DOCUMENTS

| 7,174,536 | B1* | 2/2007 | Kothari et al. | 717/109 |
| 2006/0064666 | A1* | 3/2006 | Amaru et al. | 717/100 |
| 2006/0195460 | A1* | 8/2006 | Nori et al. | 707/100 |
| 2014/0164073 | A1* | 6/2014 | Mosley et al. | 705/7.42 |
| 2014/0245163 | A1* | 8/2014 | Mubarek et al. | 715/738 |
| 2015/0120583 | A1* | 4/2015 | Zarrella | 705/317 |

OTHER PUBLICATIONS

Jie Bao, Giora Slutzki, Vasant Honavar, Privacy-Preserving Reasoning on the Semantic Web, 2007, Computer Science Technical Reports, Paper 240, pp. 1-8.*
Csilla Farkas, Alexander Brodsky, Sushil Jajodia, Unauthorized Inferences in Semistructured Databases, 2006, Information Sciences 176:3269-3299.*
Martin Knechtel, Access Restrictions to and with Description Logic Web Ontologies, 2010, Doctoral Dissertation, Dresden University of Technology (Technischen Universität Dresden), Dresden, Germany, pp. 1-139.*

(Continued)

*Primary Examiner* — Michael J Cobb
(74) *Attorney, Agent, or Firm* — Cantor Colburn LLP; Robert Bunker

(57) ABSTRACT

Techniques for generating a visual representation of a graph are described herein. The techniques may include determining a metamodel indicating relationships between objects, and determining rules for obscuring data about the objects of the metamodel. A visual representation of a graph is generated, which visual representation illustrates at least some of the data about the objects and their relationships without illustrating the obscured data.

6 Claims, 6 Drawing Sheets

(56) References Cited

OTHER PUBLICATIONS

Csilla Farkas, Amit Jain, Duminda Wijesekera, Anoop Singhal, Bhavani Thuraisingham, Semantic-Aware Data Protection in Web Services, 2006, IEEE Workshop on Web Service Security.*
Isabel F. Cruz, Rigel Gjomemo, and Mirko Orsini, A Secure Mediator for Integrating Multiple Level Access Control Policies, 2008, Proceedings of the 12th international conference on Knowledge-Based Intelligent Information and Engineering Systems (KES 2008), Part II, pp. 354-362.*
List of IBM Patents or Patent Applications Treated As Related—Date Filed: Dec. 26, 2013; 1 page.

* cited by examiner

300

400

OBSCURED RELATIONSHIP DATA WITHIN A GRAPH

CROSS-REFERENCE TO RELATED APPLICATION

This application is a continuation of U.S. patent application Ser. No. 14/141,045, filed on Dec. 26, 2013, the content of which is incorporated by reference herein in its entirety

BACKGROUND

The present disclosure relates generally to graph generation. More specifically, the techniques described herein include obscuring certain relationship data in a visual representation of a graph of related objects.

SUMMARY

In one embodiment, a method for generating a visual representation of a graph is described herein. The method includes determining a metamodel indicating relationships between objects. Rules are determined for obscuring data about the objects of the metamodel. A visual representation of the graph is generated to illustrate at least some of the data about the objects and their relationships without illustrating the obscured data.

In another embodiment, a computing device including a storage device and a processor is described herein. The storage device includes instructions that, when executed by the processor, cause the computing device to determine a metamodel indicating relationships between objects and determine rules for obscuring data about the objects of the metamodel. In embodiments, the instructions cause the computing device to generate a visual representation of the graph that illustrates at least some of the data about the objects and their relationships without illustrating the obscured data.

In yet another embodiment, a computer-readable medium comprising instructions to direct a processor to carry out operations is described herein. The operations include determining a metamodel indicating relationships between objects and rules for obscuring data about objects of the metamodel. The operations include generating a visual representation of the graph to illustrate at least some of the data about the objects and their relationships without illustrating the obscured data.

BRIEF DESCRIPTION OF THE SEVERAL VIEWS OF THE DRAWINGS

The subject matter which is regarded as the invention is particularly pointed out and distinctly claimed in the claims at the conclusion of the specification. The foregoing and other features, and advantages of the disclosure are apparent from the following detailed description taken in conjunction with the accompanying drawings in which;

DETAILED DESCRIPTION

The subject matter disclosed herein relates to techniques for generation of a graph configured to obscure at least some data about the objects and their relationships. In some scenarios, a user may need to access information of objects related to a central object, but may not access information due to privacy restrictions in a given context. For example, a user may include a doctor and the central object may be a patient. In order to correctly diagnose the patient for a given potential attribute, such as a disease, the doctor may benefit by knowing a medical history of other objects, such as siblings, parents, or relatives that are related to the patient. In this example, rules may be determined to allow the doctor to know whether relatives of the patient have the disease without revealing restricted information of relatives, such as their name, identification numbers, and the like. A visual representation of graph may be generated illustrating relationships between the patient and the patient's relatives while obscuring data that may be restricted. The graph may grant the user access to useful information for a central object and for a given potential attribute. In the example above, the doctor may see the number of relatives that have the suspected disease without revealing the identity of relatives. As discussed in more detail below, the rules may be configurable such that data is obscured based on various factors related to the context of the objects, the degree of connection between the central object and the other objects, the context of the potential attribute for which data is sought after, and the like.

A metamodel, as discussed herein, is a model specifying types of objects and relationships between them. Semantic models, such as ontologies, can be used for this purpose. Rules may be determined for how to obscure data. The metamodel also mentions roles and associates them with rules—e.g., a personal physician is a role, and a personal physician is allowed to see all a patient's data; and a researcher physician is another role and can only see certain aggregated/obscured data.

Figure 1:
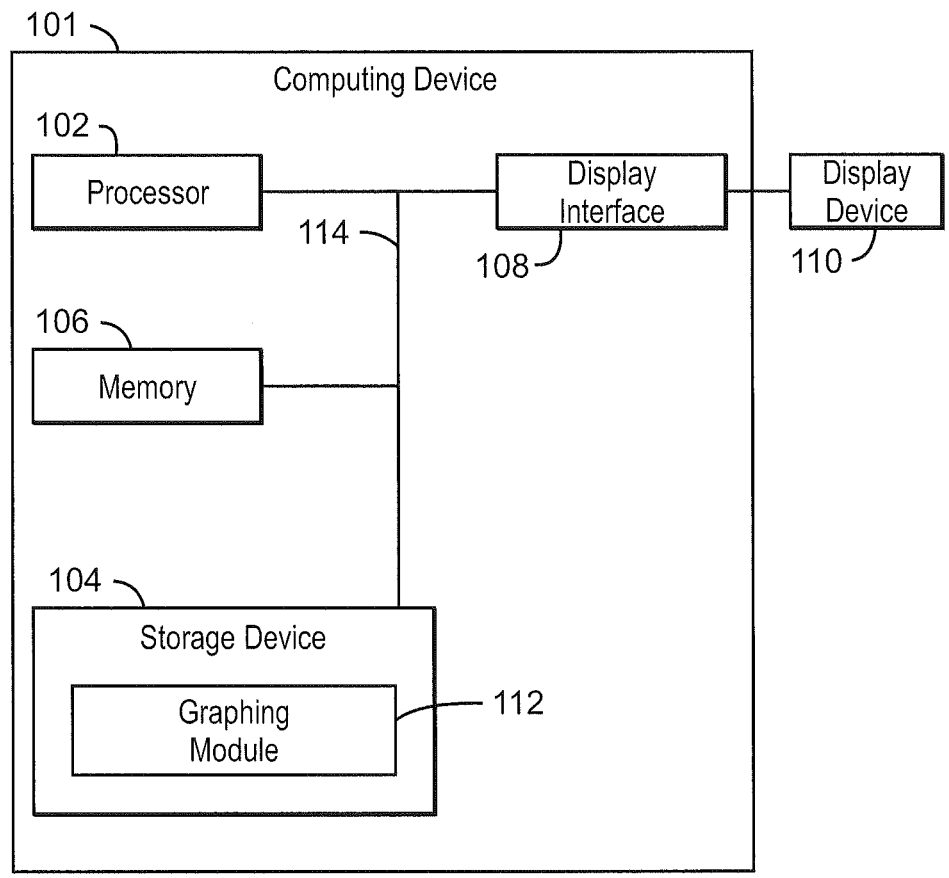
FIG. 1 is a block diagram of a computing system configured to generate a visual representation of a graph illustrating at least some of data about the objects and their relationships without illustrating obscured data in accordance with an embodiment.

FIG. 1 is a block diagram of a computing system configured to generate a visual representation of a graph illustrating at least some of data without illustrating obscured data. The computing system 100 may include a computing device 101 having a processor 102, a storage device 104 comprising a non-transitory computer-readable medium, a memory device 106, a display interface 108 communicatively coupled to a display device 110. The storage device 104 may include a graphing module 112 configured to generate a visual representation of a graph illustrating relationships between a central object and other objects without revealing private data. In embodiments, a metamodel may be determined indicating relationships between objects. Rules may be determined for obscuring data about objects of the metamodel. A visual representation of a graph may be generated that illustrates at least some of the data about the objects and their relationships without illustrating the obscured data, as discussed in more detail below.

In some embodiments, the display interface 108 may enable a user of the computing system 101 to view the visual representation of the graph via the display device 110. The display device 110 may be an external component to the computing device 101, an integrated component of the computing device 101, or any combination thereof.

The graphing module 112 may be logic, at least partially comprising hardware logic. In embodiments, the graph module 112 may be implemented as instructions executable by a processing device, such as the processor 102. The instructions may direct the processor 102 to determine the metamodel and rules for obscuring data about objects of the metamodel. The instructions may also direct the processor 102 to generate the visual representation of the graph illustrating the at least some of the data about the objects and their relationships without the obscured data.

The processor 102 may be a main processor that is adapted to execute the stored instructions. The processor 102 may be a single core processor, a multi-core processor, a computing cluster, or any number of other configurations. The memory unit 106 can include random access memory, read only memory, flash memory, or any other suitable memory systems. The main processor 102 may be connected through a system bus 114 to components including the memory 106, the storage device 104, and the display interface 108.

The block diagram of FIG. 1 is not intended to indicate that the computing device 101 is to include all of the components shown in FIG. 1. Further, the computing device 101 may include any number of additional components not shown in FIG. 1, depending on the details of the specific implementation.

Figure 2:
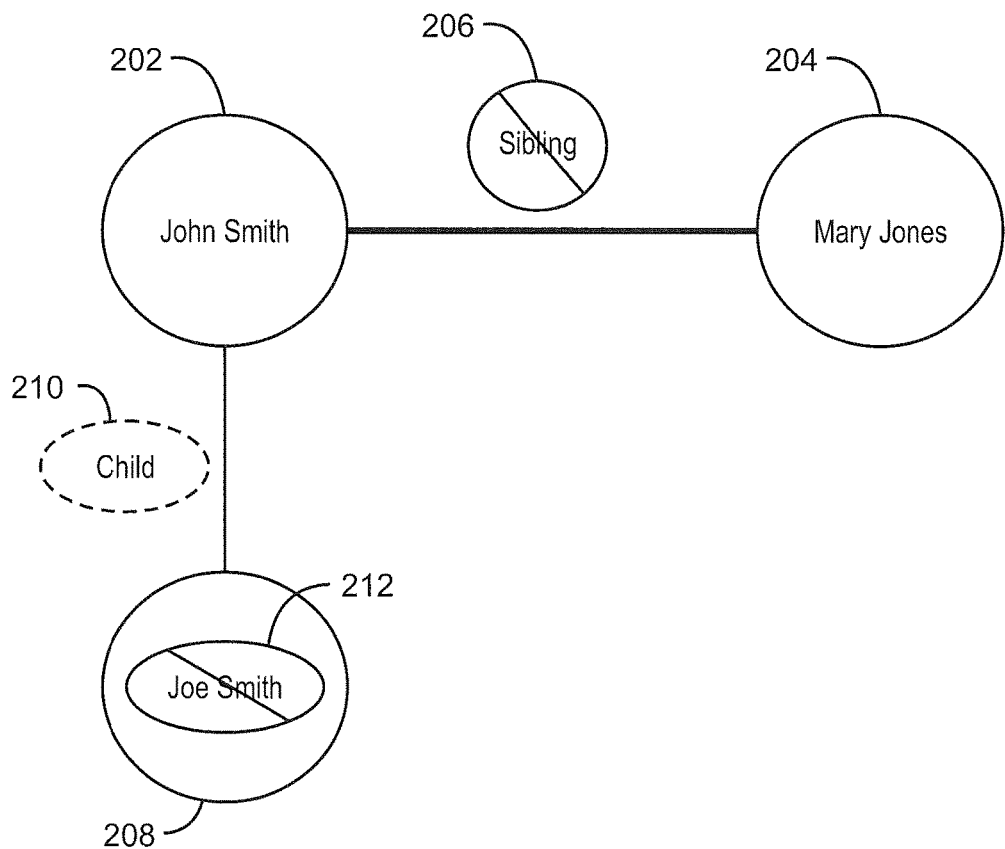
FIG. 2 is an example illustration of a graph having nodes and edges in accordance with an embodiment.

FIG. 2 is an example illustration of a graph having nodes and edges. The graph 200 is includes nodes and edges. In the example illustrated in FIG. 2, the nodes comprise people that are related to each other by a familial relationship. The central object, in the example illustrated in FIG. 2, is John Smith, as indicated by the node 202. As illustrated in FIG. 2, Mary Jones, indicated by the node 204, is related to John Smith as indicated by edge connecting the Mary Jones node 204 to the John Smith node 202. In this case, the relationship between John Smith 202 and Mary Jones 204 is a sibling relationship. The prohibition sign at 206 illustrates that the specific relationship between John Smith 202 and Mary Jones 204 may be restricted.

Without the prohibition signs, the graph 200 illustrates an embodiment of a metamodel defining relationships between related persons. The relationships in the metamodel are defined from the perspective of the central object, which in this case is John Smith 202. In other words, the metamodel indicates that Joe Smith is related to John Smith in a parent/child relationship, rather than in a nephew/aunt relationship if the metamodel was defined from the perspective of Mary Jones. In other words, the metamodel defines relationships between objects of a graph based on the relationships of the central object. Rules may be determined for obscuring the data about the relationships indicated in the metamodel, as illustrated by the prohibition signs.

As another example, the central object, John Smith 202, may have a child Joe Smith 208. While the relationship between John Smith 202 and Mary Jones 206 may be obscured by failing to provide information regarding the type of relationship as indicated at 206, the type of relationship between Joe Smith 208 and John Smith 202 may not be restricted as indicated by the dashed circle 210. However, name of John Smith's 202 children may be restricted and therefore would not be indicated in the graph 200 as illustrated by the prohibition sign 212.

Although FIG. 2 illustrates an example of familial relationships, the embodiments described herein are not restricted to familial relationships. For example, the embodiments described herein may determine a metamodel describing relationships between servers within a network. Certain information related to the servers may need to be obscured. In some scenarios, a server administrator may need to review some information regarding relationships between servers, but may be restricted from viewing information for a given server, such as a server name, or the types of data that may be provided to a given server from another server indicated in the metamodel.

In another embodiment, the visual representation of a graph generated to provide some data regarding the relationships between objects while obscuring some of the data may include legal discovery in a litigation context. For example, an opposing attorney to a corporation may be legally allowed to view the number of entities, such as subsidiary companies, related to the corporation. However, the attorney may be restricted from knowing whether the corporation owns a given entity, or whether the corporation is owned by the entity.

In any of the examples provided above, as well as other scenarios not enumerated herein, a visual representation of a graph may be generated that obscures at least some of the relationship data that may be restricted while illustrating relationship data that is not restricted. Rules may be determined for obscuring the data about the relationships indicated in the metamodel. The rules for obscuring data may depend on various factors discussed in more detail below.

Figure 3:
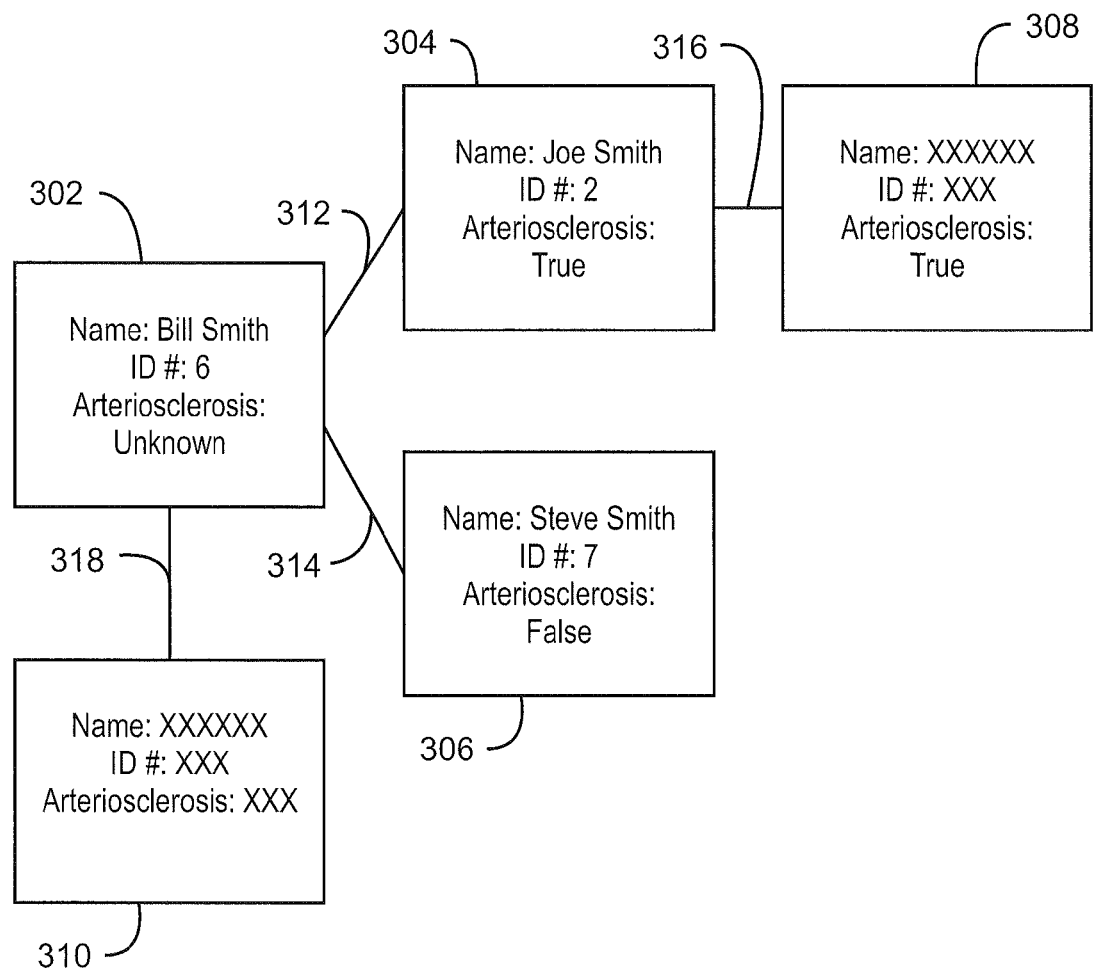
FIG. 3 is a graph illustrating relationships between a central object and having at least some data obscured in accordance with an embodiment.

FIG. 3 is a graph illustrating relationships between a central object and having at least some data obscured. The graph 300 includes a central object node 302. The graph 300 also includes other nodes 304, 306, 308, 310. In the example illustrated in FIG. 3, the central object 302 has a name, an identification (ID) number, such as a social security number, and a potential attribute for which data is sought from the relationships between the central object and the other objects including the nodes 304, 306, 308, 310. In this scenario, the potential attribute for which data is sought is the disease arteriosclerosis. Bill Smith, at central object node 302, may be related to Joe Smith, at node 304, and to Steve Smith, at node 306, as indicated by the edge 312 and edge 314, respectively. While the name, ID number, and potential attribute may be illustrated by the graph 300 in the nodes 304, 306, the nature of the relationship (e.g., sibling, parent, cousin, and the like) between central object node 302 and either 304 or 306 may be obscured. In this scenario, a user may be able to see that at least one node, such as node 304, has the potential attribute of arteriosclerosis for which information is sought for the central object.

As illustrated in FIG. 3, the node 304 may be related to node 308 as indicated by the edge 316. In this scenario, the central node 302 is related to the node 308 by a second degree relationship via the node 304. In some scenarios, the rules for obscuring data may allow first degree relationships to reveal more information than second degree relationships. In the example embodiment of FIG. 3, information including the name and ID number of node 308 may be obscured from the graph 300, while the information related to the potential attribute of arteriosclerosis is revealed as illustrated at node 308.

In some scenarios, the relationships between the central object 302 and the other nodes 304, 306, 308, 310, may be of multiple types. In the example embodiment of FIG. 3, the relationships between the central node 302 and the other nodes 304, 306, 308, 310 may be both familial and whether the central object 302 resides in the same dwelling as any of the other nodes 304, 306, 308, 310. For example, the node 310 may be a person sharing the same dwelling as indicated by the edge 318. In some scenarios, the information may be more restricted in node 310 as compared to 308 based on the type of relationship between the central node 302 and the node 310. In some examples, a couple may live together, or work together, but information related to nodes sharing the same dwelling, or same workplace, such as the node 310, may be restricted. Therefore, no information is displayed in the graph 300 regarding node 310, other than the fact that the relationship exists.

As discussed above, rules may be determined for obscuring data. The rules regarding how to obscure data may be based on the relationship type between nodes. For example, if one of two total siblings is the central object for which information related to a given disease is sought, the other sibling's identity may be deduced if they were represented as a sibling in the graph since no other siblings exist. Therefore, in some embodiments, the rules may require the sibling to be merged with parents into a first degree familial relationship node such that sensitive information related to the only other sibling may not be deduced. As another example, the relationship data may be obscured at a second degree relationship as opposed to being revealed at a first degree relationship as discussed above in relation to FIG. 3.

In some embodiments, the rules regarding obscuring data may be based on the context of an potential attribute for which information is sought. For example, a metamodel may indicate relationships between servers. The potential attribute being sought may be related only to a few servers, therefore, the graph may reveal certain information revealing the identity of those servers, while obscuring identity information of other servers in the metamodel.

In some embodiments, the rules regarding obscuring data may be based on the role of a user viewing the graph. For example, a lawyer on one side of a law suit may be allowed to view greater detail than a lawyer on an opposing side of the law suit.

In some embodiments, the rules may aggregate the data of a plurality of objects such that the potential attribute of the central object existing in at least some of the related objects may be illustrated in the graph without illustrating the obscured data. For example, the graph may provide one or more nodes illustrating an average value, such as an average blood sugar level, indicating the average existence or presence of a given potential attribute of the central object. Other techniques may be implemented such as displaying relates objects' maximum value, minimum value, summed value, and the like for a given potential attribute existing amongst the objects related to the central object. In another example, information technology systems including networked servers may be given a numerical rating for sensitivity. In this scenario, the attribute may be related to the numerical sensitivity rating, and data associated with the related objects may be displayed, such as the average, maximum, minimum, sum, and the like, without displaying any specifics about a given server amongst the networked servers.

In some embodiments, the central object may be selectable by a user of the visual representation. In other words, the central object may be changed, for example, if the user moves a focus of a graphical user interface to another object thereby shifting the perspective of the visual representation to the new object.

Figure 4:
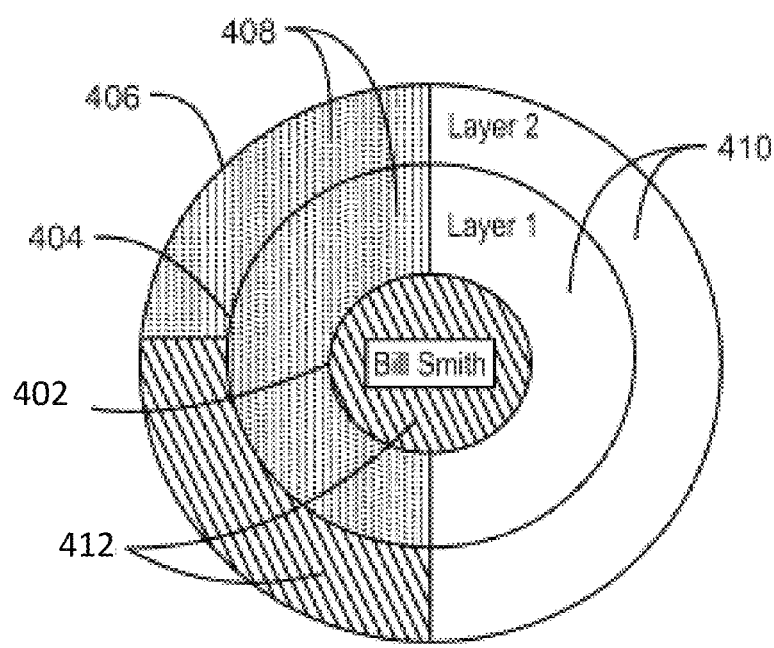
FIG. 4 is an alternative embodiment of a graph illustrating relationships between a central object and having at least some data obscured in accordance with an embodiment.

FIG. 4 is an alternative embodiment of a graph illustrating relationships between a central object and having at least some data obscured. The graph 400 includes a central object 402, a first layer 404 concentric about the central object 402, and a second layer concentric about the first layer 404 and the central object 402. In the graph 400, layers are used to illustrate different true or false statement related to a given potential attribute for which information is sought. In contrast to FIG. 3 which uses edges and nodes, the graph 400 illustrated in FIG. 4 groups all first degree connections into the first layer 404 and all second degree connections into the second layer 406. The first layer 404 includes two different shadings 408, 410. The first shading 408 in the first layer 404 is shared by the second layer 406, indicating that for a given potential attribute, half of the first layer 404 has the attribute, and a fourth of the second layer 406 has the attribute. Further, half of the first layer 404 has a second shading 410 shared by half of the second layer 406, indicating that half of the first and second layers 402, 404 do not have the attribute. In addition, a third shading 412 is meant to indicate that the attribute is unknown as illustrated in the second layer 406 and the central object 402 illustrated in FIG. 2.

Figure 5:
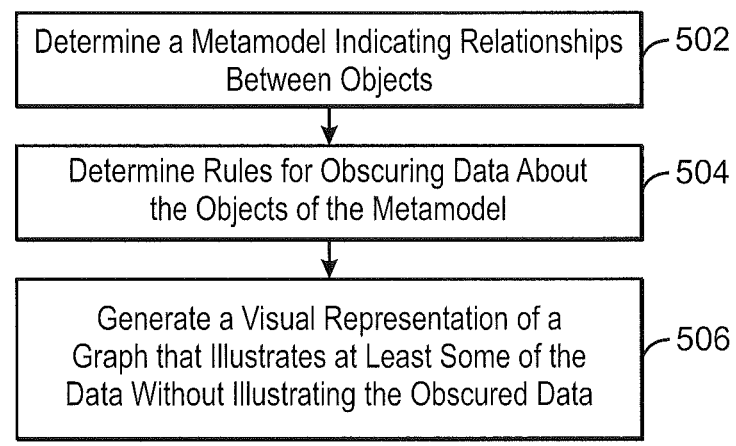
FIG. 5 is a block diagram illustrating a method of generating a graph configured to obscure at least some data regarding relationships between objects in accordance with an embodiment.

FIG. 5 is a block diagram illustrating a method of generating a graph of configured to obscure at least some data regarding relationships between objects. At block 502, the method 500 may determine a metamodel indicating relationships between objects. At block 504, rules are determined for obscuring data about objects of the metamodel. A visual representation of a graph is generated, at block 506, illustrating at least some of the data about the objects and their relationships without illustrating the obscured data.

As will be appreciated by one skilled in the art, embodiments may be implemented as a system, method or computer program product. Accordingly, embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for embodiments may be written in any combination of one or more programming languages, including an object oriented programming language such as Java, Smalltalk, C++, JavaScript, objective C and C#, or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Embodiments are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 6:
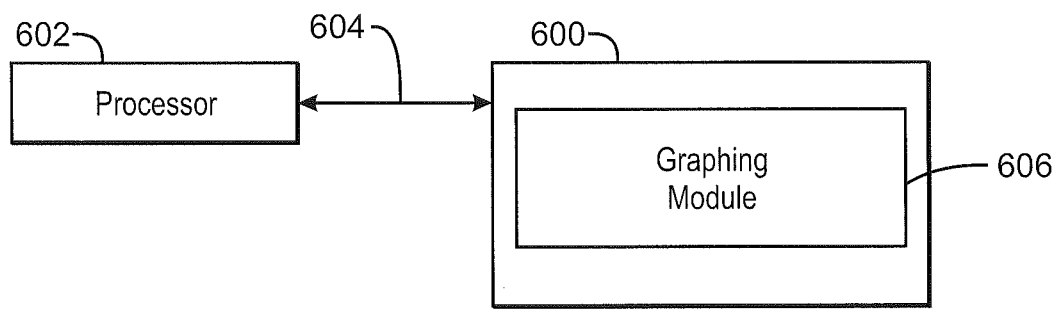
FIG. 6 is a block diagram depicting an example of a tangible, non-transitory computer-readable medium usable to form a graph configured to obscure at least some data regarding relationships between objects in accordance with an embodiment.

FIG. 6 is a block diagram depicting an example of a tangible, non-transitory computer-readable medium that can be used to form a graph configured to obscure at least some data regarding relationships between objects. The tangible, non-transitory, computer-readable medium 600 may be accessed by a processor 602 over a computer bus 604. Furthermore, the tangible, non-transitory, computer-readable medium 600 may include computer-executable instructions to direct the processor 602 to perform the steps of the current method.

The various software components discussed herein may be stored on the tangible, non-transitory, computer-readable medium 600, as indicated in FIG. 6. For example, a graphing module 606 may be configured to determine a metamodel indicating relationships between objects. The graphing module 606 may also determine rules for obscuring data related to the relationships, and related to the objects. A visual representation of a graph may be generated by the graphing module 606 that illustrates at least some of the data about the objects and their relationships without illustrating the obscured data.

The flowchart and block diagrams in the Figures illustrate the architecture, functionality, and operation of possible implementations of systems, methods and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments described herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:
determining, via a computer processor, a metamodel indicating relationships between an identified central object and objects related to the central object, wherein the relationships indicated in the metamodel are defined from the perspective of the central object and each object represents a person;
accessing data, via the computer processor, from the related objects based on their respective relationship with the central object and on a query related to a medical condition of the central object;
determining, via the computer processor, rules for obscuring accessed data about the related objects of the metamodel utilizing restrictions relating to the relationships between the central object and the related objects, wherein the rules include at least:

obscuring the data based on a role of the user viewing the graph;
obscuring the data based on a type of relationship between each of the related objects and the central object; and
obscuring the data based on a degree of connection between the central object and the related objects, with a first degree connection obscuring less data than a second degree connection;
generating, via the computer processor, a visual representation of a graph that illustrates at least some of the accessed data about the central object and their relationships to each other, wherein the visual representation comprises nodes and edges, the edges indicating the relationships between each of the related objects relative to the central object and the nodes indicating the central and related objects, wherein the visual representation of the graph obscures the accessed data by using the rules to generate the visual representation of the medical data to the user without illustrating the obscured data; and
displaying the visual representation of the graph on a display device that is communicatively coupled to the processor;
wherein when an identity of one or more related objects at a first degree connection can be determined, creating a new node at the first degree connection by merging the one or more related objects with another object at the first degree connection or moving the one or more related objects from the first degree connection to a second degree connection so as to not reveal the identity of the one or more related objects;
wherein the type of relationship includes at least one of familial relationships, working relationships, or dwelling relationships, with information related to non-familial relationships being more obscured than in the visual representation than working and dwelling relationships; and
wherein the accessed data of the related objects is aggregated into one or more nodes such that a potential attribute of the central object existing in at least some of the related objects may be illustrated in the graph without illustrating the obscured data.

2. The method of claim 1, the rules are also determined based on a context of the potential attribute.

3. The method of claim 1, wherein the central object is selectable and can be changed by the user of the visual representation of the graph.

4. A computer program product for graph generation, the computer product comprising a non-transitory computer readable storage medium having program code embodied therewith, the program code executable by a processor to perform:
determining, via the processor, a metamodel indicating relationships between an identified central object and objects related to the central object, wherein the relationships indicated in the metamodel are defined from the perspective of the central object and each object represents a person;
accessing data, via the processor, from the related objects based on their respective relationship with the central object and on a query related to a medical condition of the central object;
determining, via the processor, rules for obscuring accessed data about the related objects of the metamodel utilizing restrictions relating to the relationships between the central object and the related objects, wherein the rules include at least:
obscuring the data based on a role of the user viewing the graph;
obscuring the data based on a type of relationship between each of the related objects and the central object; and
obscuring the data based on a degree of connection between the central object and the related objects, with a first degree connection obscuring less data than a second degree connection;
generating, via the processor, a visual representation of a graph that illustrates at least some of the accessed data about the central object and their relationships to each other, wherein the visual representation comprises nodes and edges, the edges indicating the relationships between each of the related objects relative to the central object and the nodes indicating the central and related objects, wherein the visual representation of the graph obscures the accessed data by using the rules to generate the visual representation of the medical data to the user without illustrating the obscured data; and
displaying the visual representation of the graph on a display device that is communicatively coupled to the processor;
wherein when an identity of one or more related objects at a first degree connection can be determined, creating a new node at the first degree connection by merging the one or more related objects with another object at the first degree connection or moving the one or more related objects from the first degree connection to a second degree connection so as to not reveal the identity of the one or more related objects;
wherein the type of relationship includes at least one of familial relationships, working relationships, or dwelling relationships, with information related to non-familial relationships being more obscured than in the visual representation than working and dwelling relationships; and
wherein the accessed data of the related objects is aggregated into one or more nodes such that a potential attribute of the central object existing in at least some of the related objects may be illustrated in the graph without illustrating the obscured data.

5. The computer program product of claim 4, the rules are also determined based on a context of the potential attribute.

6. The computer program product of claim 4, wherein the central object is selectable and can be changed by the user of the visual representation of the graph.

* * * * *